United States Patent [19]

Kanjolia et al.

[11] Patent Number: 5,350,869
[45] Date of Patent: Sep. 27, 1994

[54] PURIFICATION OF TRIALKYLGALLIUM, SYNTHESIS OF TRIALKYLGALLIUM

[75] Inventors: Ravindra K. Kanjolia, North Andover; Benjamin C. Hui, Peabody, both of Mass.; William B. Grant, Hampton, N.H.

[73] Assignee: CVD, Incorporated, Woburn, Mass.

[21] Appl. No.: 98,483

[22] Filed: Jul. 27, 1993

[51] Int. Cl.$^5$ .............................................. C07F 5/00
[52] U.S. Cl. ........................................ 556/1; 556/129
[58] Field of Search ................................. 556/1, 129

[56] References Cited

U.S. PATENT DOCUMENTS 4,564,509  1/1986  Shealy et al. .................... 423/210.5

FOREIGN PATENT DOCUMENTS 0546617  2/1977  U.S.S.R. .

*Primary Examiner*—José G. Dees
*Assistant Examiner*—Porfirio Nazario-Gonzalez
*Attorney, Agent, or Firm*—Wayne E. Nacker; Gerald K. White

[57] ABSTRACT

Trialkylgallium is purified of group II B p-type impurities, particularly Zn, Hg, and Cd, by contacting the trialkylgallium with a metallic gallium-containing melt. Also, trialkylgallium can be produced by contacting a dialkyl group II B compound with a metallic gallium-containing melt.

12 Claims, No Drawings

PURIFICATION OF TRIALKYLGALLIUM, SYNTHESIS OF TRIALKYLGALLIUM

The present invention is directed to purification of trialkylgallium, particularly to removal of zinc from trialkylgallium. The invention further describes a novel synthesis of trialkylgallium.

BACKGROUND OF THE INVENTION

Trialkylgalliums are commonly used gallium sources in the fields of epitaxial semiconductor growth and/or processing, vapor or plasma etching, plasma deposition or thin film deposition, e.g., metalorganic chemical vapor deposition (MOCVD). Trialkylgalliums are most commonly synthesized from gallium trichloride, which often results in zinc being present in the form of dialkylzinc up to a few ppm level. Zinc is a p-type impurity and even a few ppm may be detrimental in semiconductor applications. Dialkylzinc can be very difficult to remove from trialkylgallium by common methods, such as distillation, due to the close proximity of their boiling points. For example, trimethylgallium boils at 56° C. and dimethylzinc at 46° C.

It would be desirable to remove substantially all zinc from a trialkylgallium supply, and this constitutes a primary object of the present invention. It is a further object of the present invention to synthesize trialkylgallium in a novel manner.

SUMMARY OF THE INVENTION

Zinc is removed from trialkylgallium by contacting the trialkylgallium with a metallic gallium-containing melt for a sufficient period of time to remove substantially all zinc impurities.

Trialkylgallium is produced by contacting a metallic gallium-containing melt with dialkylzinc.

DETAILED DESCRIPTION OF CERTAIN PREFERRED EMBODIMENTS

Unless otherwise noted, all amounts herein are by weight.

It is found that contacting a trialkylgallium with a metallic gallium-containing melt removes zinc and other group II B impurities, in the form of the dialkyl group II B metals by the reaction:

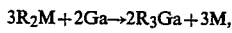

$$3R_2M + 2Ga \rightarrow 2R_3Ga + 3M,$$

where R is an alkyl moiety and M is a group II B metal, particularly Zn, Hg, and Cd. Hg and Cd are also p-type materials, undesirable impurities in many semiconductor applications. Because Zn is generally the most abundant of these impurities, the purification aspect of this invention will be defined herein in terms of zinc removal, although it will be appreciated that as Zn is being removed, Hg and Cd are removed as well. A particularly advantage of this method of purification is that the reaction product of the impurity produces the material which is being purified (the trialkylgallium) and a (non-volatile) metal. While any trialkylgallium may be purified by the method of the invention, $C_1$–$C_4$ trialkylgalliums are of most importance, particularly trimethylgallium and triethylgallium.

Zn removal is effected by contacting a metallic gallium-containing melt with the trialkylgallium for a time sufficient to reduce the content of zinc element to about 0.5 ppm (by weight) or below. (1 ppm Zn is too high for many semiconductor applications.) In fact, trialkylgallium has been purified to below detectable levels (about 0.5 ppm) by inductively coupled plasma emission spectroscopy (ICP).

U.S. Pat. No. 4,564,509 to Shealy et al., the teachings of which are incorporated by reference, describes a method of removing oxygen and water vapor from reactant gases, including trimethylgallium and triethylgallium by bubbling the gases through a melt containing gallium, indium and an oxygen-gettering metal, such as aluminum, magnesium, calcium, and lithium. This patent does not teach removal of group II B impurities. While removal of some group II B impurities would inherently result, the bubbling method described in this patent would provide far too little gas/melt contact time for removal of zinc to a 0.5 ppm level.

The melt may be simply molten gallium metal, gallium melting at 29.78° C. However, as taught in U.S. Pat. No. 4,564,509, the melting point of gallium may be lowered by the addition of metallic indium, a 16.5° C. eutectic being reached at 24.5% indium. Lesser or greater amounts of indium may be added, depending upon the melting point desired. Although indium does not react significantly with dialkyl group II B compounds, it may help promote the reaction with gallium; accordingly, it is preferred that the melt contain at least about 8–10% indium. Indium could be present at a very high level, e.g., up to about 60%, however, as gallium metal is the reacting species of the melt, there is no apparent advantage in providing indium above its eutectic level. The melt could also contain an oxygen-gettering metal, as per the above-referenced U.S. Pat. No. 4,564,509, provided the metal not react with the dialkyl Group II B impurities to produce volatile impurities. Aluminum does not react with dialkyl group II B impurities.

The amount of contact time of the trialkylgallium with the metallic gallium-containing melt will depend upon several factors, including the initial level of impurities, the desired final level of impurities, the contact temperature and the method of contact. A convenient contact method is to reflux the trialkylgallium in the presence of the (preferably agitated) melt. Trimethylgallium may be refluxed at its boiling temperature (56° C.). Triethylgallium has a boiling point of 146.2° C., however, due to its tendency to be unstable at this temperature, refluxing at reduced pressure and temperature is preferred. An example of a useful reflux condition for triethylgallium is 92° C. at 138 mm Hg. Refluxing for about 10 min. may be sufficient to reduce zinc levels to 0.5 ppm; however, to ensure almost complete zinc removal, refluxing for 1 to 3 hours is typical.

While the invention has been described in terms of purification of trialkylgallium compounds, other $C_1$–$C_4$ trialkyl group III A compounds, particularly trialkylindium and trialkylaluminum compounds, can be purified of group II B elements in the form of dialkyl group II B compounds by the method of the present invention, i.e., contacting the material with a metallic gallium-containing melt. However, the conversion product is a trialkylgallium present as a low level impurity which may or may not be significant. The trialkylgallium impurity should not be significant if gallium is being co-deposited with the group III A element of the compound being purified.

The above chemical equations also show that trialkylgallium can be produced by contacting a metallic gallium-containing melt with dialkyl group II B compound, particularly a $C_1$–$C_4$ group II B compound. While this is incidental in the purification reaction, dialkyl group II B compound may be treated with a metallic-gallium-containing melt, producing trialkylgallium and the elemental form of the metal. The usefulness of this as a synthetic method depends upon economics of the method. It is probably most useful for forming triethylgallium from diethylzinc as diethylzinc is an abundant, inexpensive material. Also, trimethylgallium may potentially be economically produced. The dialkyl group II B compound is contacted with a metallic gallium-containing melt for a time sufficient to react substantially all of the dialkyl group II B compound with the gallium to produce trialkyl gallium. The melt must, of course, contain at least a stoichiometric amount of gallium, but preferably, the gallium is provided in significant excess.

The invention will now be described in greater detail by way of specific examples.

EXAMPLE 1

Under an inert atmosphere, dimethylzinc (3 grams) was transferred into the trimethylgallium (56 grams), and the resulting mixture was swirled for 1 min. No reaction was observed. A sample (A) was pulled from the resulting mixture for ICP (inductively coupled plasma spectroscopy) analysis. 28 grams of GaInAl melt was then added to this mixture of dimethylzinc and trimethylgallium and swirled for 1 min. Within 1 hr. a gray film was seen to have plated onto the surface of the melt, indicating formation of a film of metallic zinc. The flask was left stirring outside the glovebag under inert atmosphere overnight, and another sample (B) was collected afterwards.

Analysis of the starting mixture (sample A) showed high levels of zinc, beyond the upper range of the instrument. By weight, the mixture was approximately 5% dimethyl zinc. The analysis of the mixture after treatment (sample B) indicated nondetectable levels of zinc.

EXAMPLE 2

125 grams of trimethylgallium was spiked with approximately 5 microliters of dimethylzinc to produce a solution yielding approximately 40 ppm zinc in the gallium matrix. An analytical sample was collected and the remaining solution was treated with gallium/indium/aluminum melt with a melt to trimethylgallium ratio of about 1:2 (wt/wt). The trimethylgallium was allowed to stir over the melt for 12 hrs., at which time another analytical sample was taken. Both samples were analyzed by ICP. The untreated sample showed a zinc level of greater than 20 ppm. The treated sample showed an undetectable level of zinc.

EXAMPLE 3

Synthesis Of TMG Dimethylzinc And Ga/In/Al Melt

Gallium-Indium-Melt (100 g, 1.28 mole Ga metal) is weighed in a 250 ml 3-neck round bottom flash in an inert atmosphere. To the melt is added 95 g of $Me_2Zn$ (1 mole) at room temperature. The reaction mixture is heated to reflux until the shiny melt is covered by the gray zinc dust (8–10 hours). The final product is distilled out from the reaction mixture via a fractionating column. The product is characterized by H-1 NMR and ICP analysis.

What is claimed is:

1. A method of removing group II B impurities in the form of dialkyl group II B compounds from a trialkyl group III A compound having unacceptably high levels of said impurities, including zinc impurities, the method comprising contacting said trialkyl group III A compound with a metallic gallium-containing melt which comprises at least about 10 wt. % indium for a time sufficient to reduce the level of zinc to about 0.5 ppm or below.

2. A method according to claim 1, wherein said trialkyl group III A compound is contacted with said melt for sufficient time to reduce the level of zinc to about 0.05 ppm or below.

3. A method according to claim 1 wherein said trialkyl group III A compound is a trialkylgallium.

4. A method according to claim 1 wherein said melt further contains an oxygen-gettering metal.

5. A method according to claim 4, wherein said gettering metal is aluminum.

6. A method of removing group II B impurities in the form of dialkyl group II B compounds from a trialkyl group III A compound having unacceptably high levels of said impurities, including zinc impurities, the method comprising contacting said trialkyl group III A compound with a metallic gallium-containing melt which further contains an oxygen-gettering metal for a time sufficient to reduce the level of zinc to about 0.5 ppm or below.

7. A method according to claim 6 wherein said trialkyl group III A compound is contacted with said melt for sufficient time to reduce the level of zinc to about 0.05 ppm or below.

8. A method according to claim 6 wherein said gettering metal is aluminum.

9. A method according to claim 6 wherein said trialkyl group III A compound is a trialkylgallium.

10. A method of producing a trialkylgallium comprising contacting a dialkyl group II B compound with a melt containing at least a stoichiometric amount of gallium for a time sufficient to react substantially all of said dialkyl group II B compound with gallium to produce trialkylgallium and metallic group II B element.

11. A method according to claim 10 wherein said dialkyl group II B compound is dialkylzinc.

12. A method according to claim 11 wherein said dialkylzinc is dimethylzinc or diethylzinc.

* * * * *